US005824497A

United States Patent [19]
Andrews et al.

[11] Patent Number: 5,824,497
[45] Date of Patent: Oct. 20, 1998

[54] HIGH EFFICIENCY TRANSLATION OF MRNA MOLECULES

[75] Inventors: David W. Andrews; Martin John Glenton Hughes, both of Hamilton; Akaterini Vassilakos, Toronto, all of Canada

[73] Assignee: McMaster University, Hamilton, Canada

[21] Appl. No.: 386,921

[22] Filed: Feb. 10, 1995

[51] Int. Cl.$^6$ ............................ C12P 21/02; C07H 21/04; C12N 15/67

[52] U.S. Cl. ..................... 435/69.1; 435/71.1; 435/71.2; 435/183; 536/23.1; 536/24.1; 536/24.2

[58] Field of Search ................... 435/69.1, 71.1, 435/71.2, 183; 536/23.1, 24.1, 24.2; 935/33, 34, 38, 44

[56] References Cited

U.S. PATENT DOCUMENTS

| | | | |
|---|---|---|---|
| 4,716,112 | 12/1987 | Panayotatos | 435/69.1 |
| 4,740,461 | 4/1988 | Kaufman | 435/69.1 |
| 5,079,159 | 1/1992 | Kaufman | 435/226 |
| 5,149,635 | 9/1992 | Gillies | 435/69.1 |
| 5,362,865 | 11/1994 | Austin | 536/24.1 |
| 5,378,619 | 1/1995 | Rogers | 435/172.3 |
| 5,424,412 | 6/1995 | Brown et al. | 536/24.1 |

OTHER PUBLICATIONS

Cigan, A.M., and T.F. Donahue. (1987) Gene 59, 1–18.
Kozak, M. (1988) J. Cell Biol. 107, 1–7.
Lodish, H.F. (1976) Ann. Rev. Biochem. 45, 39–72.
Liebhaber, S.A., F. Cash and S.S. Eshleman. (1992) Journal of Molecular Biology 226, 609–621.
Sorenson, M.A., C.G. Kurland and S. Pedersen. (1989).
Sharp, P.M., and K.M. Devine. (1989) Nucleic Acids Res. 17, 5029–5039.
Baim, S.B. and F. Sherman. (1988) Mol. Cell. Biol. 8, 1591–1601.
Doohan, J.P. and C.E. Samuel. (1992) Virology 186, 409–425.
Kim, J., P.G. Klein and J.E. Mullet. (1991) J. Biol. Chem. 266, 14931–14938.
Kim, J., M.J. Hollingsworth. (1992) Anal. Biochem. 206, 183–188.
Rabinovich, Y.M. and M.O. Kreinin. (1991) Biochimica et Biophysica Acta 1089, 193–196.
Young, J.H.C., A. Vassilakos and D.W. Andrews, submitted.
Saini, K.S., I.C. Summerhayes and P. Thomas (1990) Mol. Cell. Biochem. 96, 15–23.
Jackson, R.J. (1993) Cell 74, 9–14.
Drummond, D.R., J. Armstrong and A. Colman. (1985) Nucleic Acids Res. 13, 7375–7394.
Nudel, U., H. Soreq and U.Z. Littauer. (1976) Eur. J. Biochem. 64, 115–121.
Bernstein, P. and J. Ross. (1989) TIBS 14, 373–377.
Galili, G., E.E. Kawata, L.D. Smith and B.A. Larkins (1988) J. Biol. Chem. 263, 5764–5770.
Jackson, R.J. and N. Standart. (1990) Cell 62, 15–24.
Wickens, M. (1990) TIBS 15, 320–324.

Laird–Offringa, I.A., C.A. deWit, P. Elfferich and A.J. van der Eb. (1990) Mol. Cell. Biol. 10, 6132–6140.
Aharon, T., and R.J. Schneider. (1993) Mol. Cell. Biol. 13, 1971–1980.
Ratnasabapathy, R., S.L. Hwang and D.L. Williams. (1990) J. Biol. Chem. 265, 14050–14055.
Saini, K.S. and I.C. Summerhayes. (1991) Biochem. Cell. Biol. 69, 415–417.
Brawerman, G. (1989) Cell 57, 9–10.
Pelham, H.R.B. (1978) Eur. J. Biochem. 85, 457–462.
Pelletier, J. and N. Soneneberg. (1988) Nature 334, 320–325.
Jobling, S.A. and L. Gehrke . (1987) Nature 325, 622–625.
Jobling, S.A., C.M. Cuthbert, S.G. Rogers, R.T. Fraley and L. Gehre. (1988) Nucleic Acids Res. 16, 4483–4498.
Johansen, H., D. Schumperli and M. Rosenberg. (1984) Proc. Natl. Acad. Sci. USA 81, 7698–7702.
Elroy–Stein, O., T.R. Fuerst and B. Moss. (1989) Proc. Natl. Acad. Sci. USA 86, 6126–6130.
Gallie, D.R., D.E. Sleat, J.W. Watts, P.C. Turner and T.M.A. Wilson. (1987) Nucleic Acids Res. 15, 3257–3273.
Gallie, D.R., D.E. Sleat, J.W. Watts, P.C. Turner and T.M.A. Wilson. (1987) Nucleic Acids Res. 15, 8693–8711.
Berkner, K.L. and P.A. Sharp. (1985) Nucleic Acids Res. 13, 841–856.
Curran, J. and D. Kolakofsky. (1989) EMBO J. 8, 521–526.
Lazarus, P. (1992) Oncogene 7, 1037–1041.
Tyc, K., M. Konarska, H.J. Gross and W. Filipowicz. (1984) FEBS 140, 503–511.
Falcone, M. and D.W. Andrews. (1991) Mol. Cell. Biol. 11, 2656–2664.
Andrews, M.T. (1989) Promega Notes No. 17:1.
Gurevich, V.V., I.D. Pokrovskaya, T.A. Obuhkova and S.A. Zozulya. (1991) Anal. Biochem. 195, 207–213.
Simon, K., E. Perara and V.R. Lingappa. (1987) J. Cell Biol. 104: 1165–1172.
Tajima, S., L. Lauffer, V.L. Rath and P. Walter. (1986) J. Cell Biol. 103, 1167–1178.
Schagger, H. and G. von Jagow. (1987) Anal. Biochem. 166, 368–379.
Kozak, M. (1978) Cell 44, 283–292.
Kozak, M. (1987) Nucleic Acids Res. 15, 8125–8148.
Kozak, M. (1989) J. Cell Biol. 108, 229–241.
Fox, C.A. and M. Wickens. Genes Dev. 4, 2287–2298.
Narayan, P., Ludwiczak, R.L., Goodwin, E.C. and Rottman, F.M. (1994) Nucleic Acids Res. 22, 419–426.

(List continued on next page.)

*Primary Examiner*—David Guzo
*Assistant Examiner*—Nancy J. Degen
*Attorney, Agent, or Firm*—Sim & McBurney

[57] ABSTRACT

An increased level of translation of a selected mRNA molecule is effected by coupling specific nucleotide sequences at the 5'- and 3'-ends of a nucleic acid molecule transcribable to or which itself is the mRNA molecule. The nucleotide sequence at the 5'-end is effective to increase the rate of translation initiation of the mRNA molecule in a cell while the nucleotide sequence at the 3'-end is effective to increase the period of translation of the mRNA molecule in a cell.

19 Claims, 6 Drawing Sheets

OTHER PUBLICATIONS

Vera, J.C. and O.M. Rosen. (1990) Mol. Cell. Biol. 10, 743–751.

Grens et al "The 5'–and 3'–Untranslated Regions of OrnUthine Decarboxylase mRNA Affect the Translational Efficiency" J Biol Chem. 265(20) 11810–11816 1990.

Sheets et al "The 3'–Untranslated Regions of C–MOS and Cyclin mRNAs Stimulat Translation by Regulating Cytoplasmic PolyAdenylation" Genes & Devel. 8 926–938 1994.

Gallie et al. "Post Transcriptional Regulation In Higher Eukaryotes: The Role of the Repoter Gene in Controlling Expression" Mol GenGenet 228 258–264 1991.

Gallie et al. "The Role of The 3' Untranslated Region of Non–Polyadenylated Plant Viral mRNAs in Regulating Translational Efficiency" Gene 142 159–165 1994.

Timmer et al. "The 5'–and 3'–Untranslated Regions of Satellite Tobacco Necrosis Virus RNA Affect Translational Efficiency . . . " J Biol Chem 268(13) 9504–9510 1993.

Kruys et al. "The 3' Untranslated Region of The Human Interferons mRNA has an Inhibitory Effect on Translation" Proc Natl Acad Sci 84 6030–6034 1987.

Falcone et al "Both the 5' Untranslated Region & the Sequences Surrounding the Start Site Contribute to Efficient Initiation of Translation In Vitro" Mol Cell Biol 11(5) 2656–2664 1991.

Sasavage et al "Nucleotide Sequence of Bovine Prolactin Messenger RNA" J Biol Chem 257(2) 678–681 1982.

Paris et al. "Maturation Specific Polyadenylation and Translational Control . . . " Mol Cell Biol 10 5634–5645 1990.

Caput et al. "Identification of a Common Nucleotide Sequence in the 3' Untranslated Region of mRNA Molecules . . . " Proc Natl. Acad. Sci 83 1670–1674 1986.

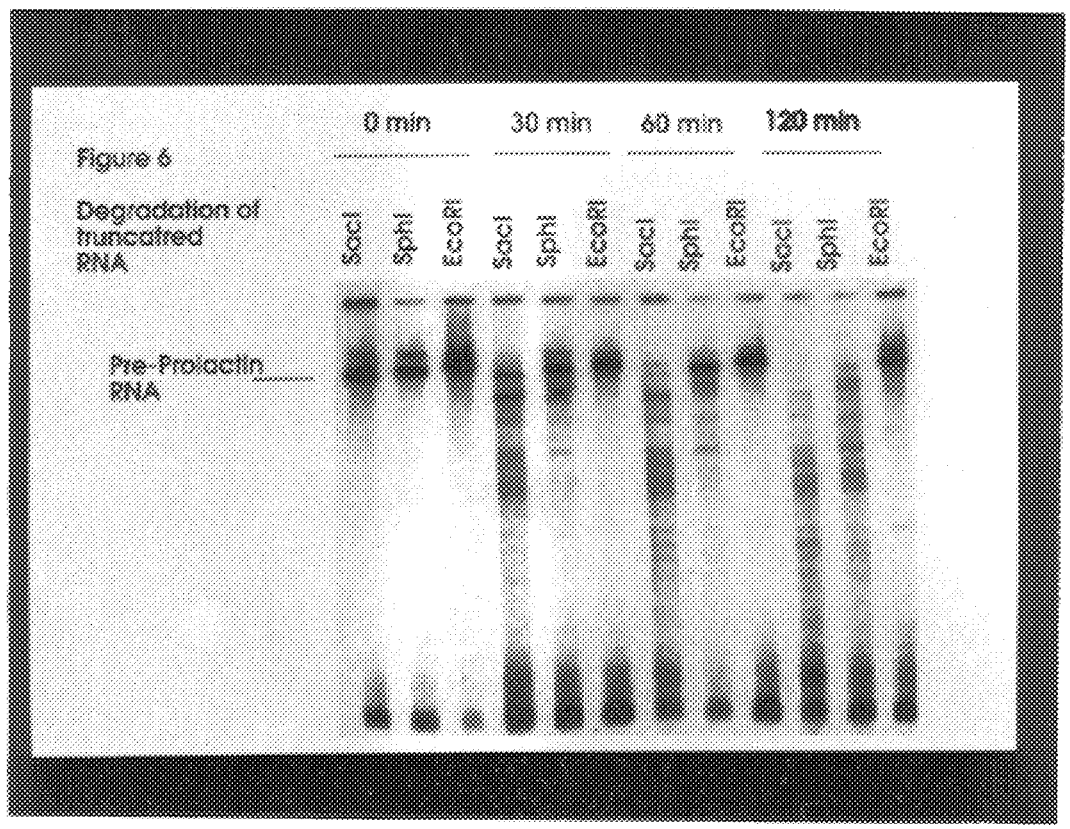
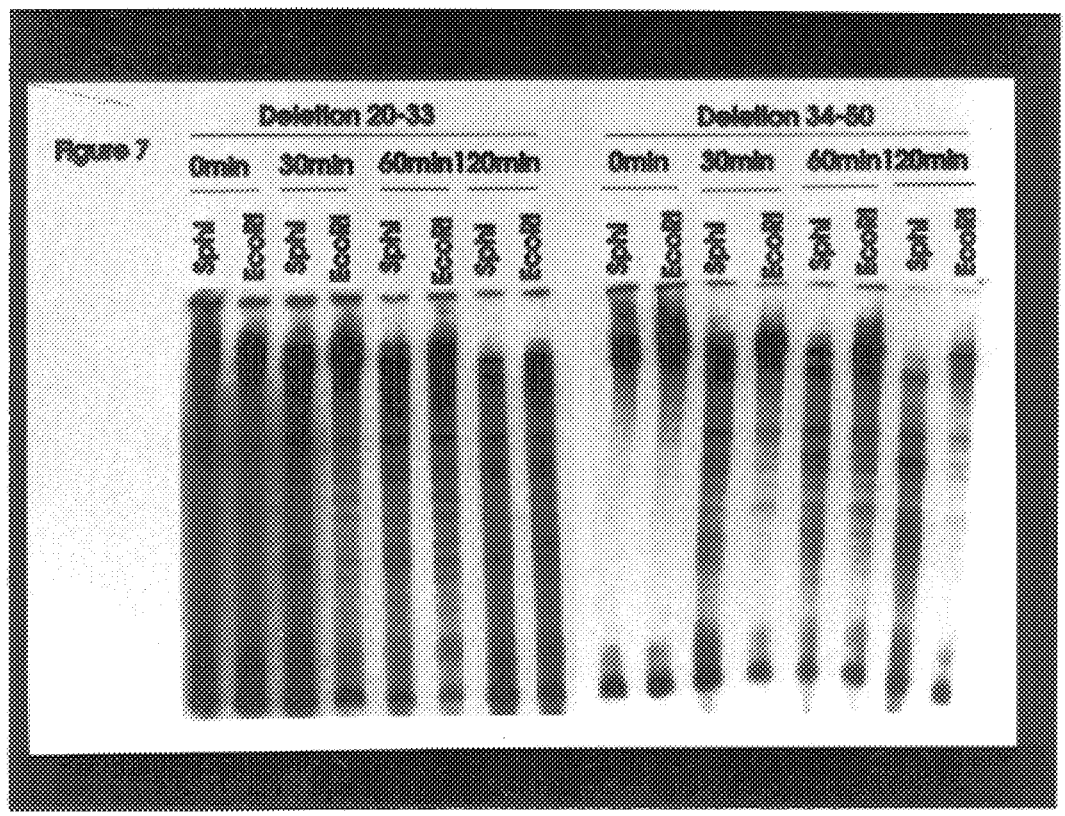

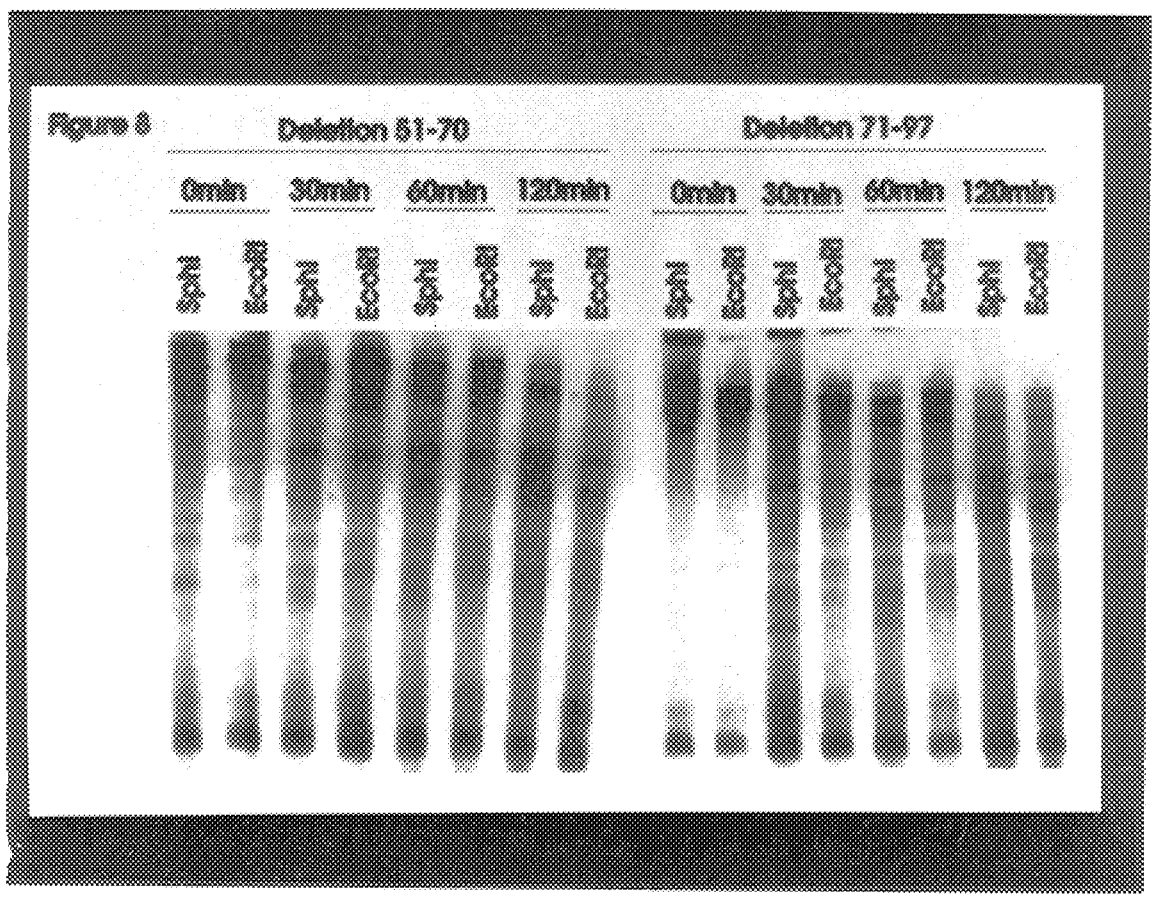

LEADER
NAME                    LEADER SEQUENCE

SD
ATTTAGGTGACACTATAGAATACAAGCTCATGG
  SP6 PROMOTOR

KD
ATTTAGGTGACACTATAGAATACAAGCTGATCTACCATGG
  SP6 PROMOTOR                      NCOI

UTR
ATTTAGGTGACACTATAGAATACAAGCTTGCVTTGTTCTTTTTGCAGAAGCTCAGAATAAACGCTCAACTTTGGCAGATCCATGG
  SP6 PROMOTOR             HINDIII        XENOPUS B-GLOBIN 5' UTR            NCOI

UTK
ATTTAGGTGACACTATAGAATACAAGCTTGCVTTGTTCTTTTTGCAGAAGCTCAGAATAAACGCTCAACTTTGGCAGATCTACCATGG
  SP6 PROMOTOR             HINDIII        XENOPUS B-GLOBIN 5' UTR            BGLII   NCOI

FIG.9

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 236 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AACAACAACU  GCUAACGAGC  UCGUAAGCCC  ACAUUCCAUC  CUUUCCAUUU  CUGAGAUGGU      60

UCUUAAUGAU  CCAUUCCCUG  GCAAACUUCU  CUGAGCUUUA  UAGCUUUGUA  AUGCAUGCUU     120

GGCUCUAAUG  GGUUUCAUCU  UAAAUAAAAA  CAGACUCUGU  AGCGAUGUCA  AAAUCUAAAA     180

AAAAAAAAAA  AAACCCCCCC  CCCCUGCAGG  UCGACUCUAG  AGGAUCCCG   GAAUUC         236
```

( 2 ) INFORMATION FOR SEQ ID NO:2:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CGAGCUCGUA  AGCCCACAUU  CCAUCCUUUC  CAUUUCUGAG  AUGGUUCUUA  AUGAUCCAUU     60

CCCUGGCAAA  CUUCUCUGAG  CUUUAUAGCU  UUGUAAUGCA  UGCUUGGCUC  UAAUGGGUUU    120

CAUCUUAAAU  AAAAACAGAC  UCUGUAGCGA  UGUCAAAAUC  U                        161
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AUGAUCCAUU  CCCUGGCAAA  CUUCUCUGAG  CUUUAUAGCU  UUGUAAU                   47
```

( 2 ) INFORMATION FOR SEQ ID NO:4:

( i ) SEQUENCE CHARACTERISTICS:
        ( A ) LENGTH: 197 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CGAGCUCGUA  AGCCCACAUU  CCAUCCUUUC  CAUUUCUGAG  AUGGUUCUUA  AUGAUCCAUU     60

CCCUGGCAAA  CUUCUCUGAG  CUUUAUAGCU  UUGUAAUGCA  UGCUUGGCUC  UAAUGGGUUU    120
```

```
CAUCUUAAAU   AAAAACAGAC   UCUGUAGCGA   UGUCAAAAUC   UAAAAAAAAA   AAAAAAACC        180

CCCCCCCCCU   GCAGGUC                                                              197
```

( 2 ) INFORMATION FOR SEQ ID NO:5:

( i ) SEQUENCE CHARACTERISTICS:
        ( A ) LENGTH: 138 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CGAGCUCGUA   AGCCCACAUU   CCAUCCUUUC   CAUUUCUGAG   AUGGUUCUUA   AUGAUCCAUU        60

CCCUGGCAAA   CUUCUCUGAG   CUUUAUAGCU   UUGUAAUGCA   UGCUUGGCUC   UAAUGGGUUU        120

CAUCUUAAAU   AAAAACAG                                                             138
```

( 2 ) INFORMATION FOR SEQ ID NO:6:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
CGAGCUCGUA   AGCCCACAUU   CCAUCCUUUC   CAUUUCUGAG   AUGGUUCUUA   AUGAUCCAUU        60

CCCUGGCAAA   CUUCUCUGAG   CUUUAUAGCU   UUGUAAUG                                   98
```

( 2 ) INFORMATION FOR SEQ ID NO:7:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
CGAGC                                                                              5
```

( 2 ) INFORMATION FOR SEQ ID NO:8:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CGAGCUCGUA   AGCCCACAUU   UCUGAGAUGG   UUCUUAAUGA   UCCAUUCCCU   GGCAAACUUC        60

UCUGAGCUUU   AUAGCUUUGU   AAUG                                                    84
```

( 2 ) INFORMATION FOR SEQ ID NO:9:

( i ) SEQUENCE CHARACTERISTICS:
        ( A ) LENGTH: 147 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
CGAGCUCGUA   AGCCCACAUU   UCUGAGAUGG   UUCUUAAUGA   UCCAUUCCCU   GGCAAACUUC        60

UCUGAGCUUU   AUAGCUUUGU   AAUGCAUGCU   UGGCUCUAAU   GGGUUUCAUC   UUAAAUAAAA        120
```

ACAGACUCUG UAGCGAUGUC AAAAUCU        147

( 2 ) INFORMATION FOR SEQ ID NO:10:

( i ) SEQUENCE CHARACTERISTICS:
    ( A ) LENGTH: 161 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

CGAGCUCGUA AGCCCACAUU CCAUCCUUUC CAUUUCUGAG AUGGUUCUUA AUGAUCCAUU        60

CCCUGGCAAA CUUCUCUGAG CUUUAUAGCU UUGUAAUGCA UGCUUGGCUC UAAUGGGUUU        120

CAUCUUAAAU AAAAACAGAC UCUGUAGCGA UGUCAAAAUC U        161

( 2 ) INFORMATION FOR SEQ ID NO:11:

( i ) SEQUENCE CHARACTERISTICS:
    ( A ) LENGTH: 144 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CGAGCUCGUA AGCCCACAUU CCAUCCUUUC CAUAUGAUCC AUUCCCUGGC AAACUUCUCU        60

GAGCUUUAUA GCUUUGUAAU GCAUGCUUGG CUCUAAUGGG UUUCAUCUUA AAUAAAAACA        120

GACUCUGUAG CGAUGUCAAA AUCU        144

( 2 ) INFORMATION FOR SEQ ID NO:12:

( i ) SEQUENCE CHARACTERISTICS:
    ( A ) LENGTH: 78 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

CGAGCUCGUA AGCCCACAUU CCAUCCUUUC CAUUUCUGAG AUGGUUCUUA CUUCUCUGAG        60

CUUUAUAGCU UUGUAAUG        78

( 2 ) INFORMATION FOR SEQ ID NO:13:

( i ) SEQUENCE CHARACTERISTICS:
    ( A ) LENGTH: 141 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

CGAGCUCGUA AGCCCACAUU CCAUCCUUUC CAUUUCUGAG AUGGUUCUUA CUUCUCUGAG        60

CUUUAUAGCU UUGUAAUGCA UGCUUGGCUC UAAUGGGUUU CAUCUUAAAU AAAAACAGAC        120

UCUGUAGCGA UGUCAAAAUC U        141

( 2 ) INFORMATION FOR SEQ ID NO:14:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

CGAGCUCGUA AGCCCACAUU CCAUCCUUUC CAUUUCUGAG AUGGUUCUUA AUGAUCCAUU        60

CCCUGGCAAA 70

(2) INFORMATION FOR SEQ ID NO:15:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO:15:

CGAGCUCGUA AGCCCACAUU CCAUCCUUUC CAUUUCUGAG AUGGUUCUUA AUGAUCCAUU 60

CCCUGGCAAA GCAUGCUUGG CUCUAAUGGG UUUCAUCUUA AAUAAAAACA GACUCUGUAG 120

CGAUGUCAAA AUCU 134

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:16:

ATTTAGGTGA CACTATAGAA TACAAGCTCA TGG 33

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:17:

ATTTAGGTGA CACTATAGAA TACAAGCTGA TCTACCATGG 40

(2) INFORMATION FOR SEQ ID NO:18:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:18:

ATTTAGGTGA CACTATAGAA TACAAGCTTG CTTGTTCTTT TTGCAGAAGC TCAGAATAAA 60

CGCTCAACTT TGGCAGATCC ATGG 84

(2) INFORMATION FOR SEQ ID NO:19:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:19:

ATTTAGGTGA CACTATAGAA TACAAGCTTG CTTGTTCTTT TTGCAGAAGC TCAGAATAAA 60

CGCTCAACTT TGGCAGATCT ACCATGG 87

(2) INFORMATION FOR SEQ ID NO:20:

(i) SEQUENCE CHARACTERISTICS:

(A) LENGTH: 7 base pairs
            (B) TYPE: nucleic acid
            (C) STRANDEDNESS: single
            (D) TOPOLOGY: linear (xi) SEQUENCE DESCRIPTION: SEQ ID NO:20:

ACCAUGG                                                                                        7

(2) INFORMATION FOR SEQ ID NO:21:

(i) SEQUENCE CHARACTERISTICS:
            (A) LENGTH: 7 base pairs
            (B) TYPE: nucleic acid
            (C) STRANDEDNESS: single
            (D) TOPOLOGY: linear (xi) SEQUENCE DESCRIPTION: SEQ ID NO:21:

CCCAUGG                                                                                        7

HIGH EFFICIENCY TRANSLATION OF MRNA MOLECULES

FIELD OF INVENTION

The present invention relates to the translation of messenger RNA (mRNA) molecules in cells and, in particular, to improvements in the efficiency thereof.

BACKGROUND TO THE INVENTION

The translational efficiency of mRNA has been shown to be due to several factors, including the 5' cap structure, the 5' leader sequence and sequences immediately surrounding the initiation codon (refs. 1 to 3—Throughout this specification, various references are referred to in parenthesis to more fully describe the state of the art to which this invention pertains. Full bibliographic information for each citation is found at the end of the specification, immediately following the claims. The disclosures of these references are hereby incorporated by reference into the present disclosure). These sequences largely determine both the rate and the fidelity of initiation of translation in vitro and in vivo. More recently sequences in the coding region have also been implicated in translational efficiency (refs. 4 to 12).

The relative abundance of an mRNA coding for a given gene product can also influence the amount of protein synthesized. The abundance of a specific mRNA species is determined both by the rate of transcript synthesis as well as the stability of the processed and transported molecule within the cytoplasm (ref. 13). The 3' untranslated region (UTR) of RNA molecules consists of a stretch of nucleotides usually containing methylation and polyadenylation sites. In most active cell systems, the RNA's are capped at the 3' end with a poly (A) stretch. The UTR is thought to play several roles in translational regulation, including the control of translational initiation, control of translation during growth and differentiation of cells and RNA stability (ref. 14). In particular, the poly A tail, found on most eukaryotic mRNA species, has been shown to be a determinant of stability for many mRNAs (refs. 15 to 17). While there is evidence for the involvement of polyadenylation in stabilizing transcripts in *Xenopus oocytes*, recent evidence also suggests that the poly A tail together with poly A binding protein may also be involved in increasing the efficiency of translation initiation for some mRNAs (refs. 15, 18 and 19). In addition, recent evidence suggests that polyadenylation and de-adenylation mechanisms are involved in the activation and inactivation of mRNA translation, (masking and unmasking), which occurs during *oocyte* maturation (ref. 20).

Since most mRNAs routinely are polyadenylated, other mechanisms may contribute to the observed differences in the stability of certain mRNAs in eukaryotic cells. Evidence for gene specific regulatory mechanisms comes from the characterization of de-stabilization sequences in the 3' UTRs of cellular proto-oncogenes and of stabilization sequences present in the α-globin 3' UTR (refs. 14 and 21).

The analysis of UTR sequences has proven useful for the development of expression vectors capable of increasing the synthesis of foreign coding regions in vitro and in vivo (refs. 26 to 38). The inventors have previously described a semi-synthetic 5' leader sequence (termed UTK) containing the Xenopus β-globin 5' UTR fused to an appropriately positioned consensus sequence for translation initiation. The UTK leader has been found to improve the translation efficiency of every coding region tested to date, in both reticulocyte lysate (ref. 38) and wheat germ extract cell free translation systems.

It would be desirable to improve the level of translation of mRNA molecules in cells, particularly prokaryotic and eukaryotic cells.

SUMMARY OF INVENTION

The present invention provides a novel method for increasing the level of translation of mRNA molecules by the employment of a combination of specific nucleotide sequences operatively coupled to the 5' and 3' ends of mRNA molecules.

Accordingly, in one aspect, the present invention provides a method of translating a selected mRNA molecule to provide an increased level of translation thereof, which comprises:

coupling to a nucleic acid molecule transcribable to or which itself is an mRNA molecule at the 5'-end thereof a first nucleotide sequence effective to increase the rate of translation initiation of said mRNA molecule in a cell, coupling to said nucleic acid molecule at the 3'-end thereof a second nucleotide sequence effective to increase the period of translation of said mRNA molecule in a cell, and effecting translation of said mRNA molecule in said cell.

In one embodiment of this aspect of the invention, the second nucleotide sequence comprises a nucleotide sequence of the 3'-UTR of prolactin, as shown in FIG. 2 described below, in particular, at least a portion of the 3'-UTR of prolactin contained within nucleotide 51 to nucleotide 97. Alternatively, the second nucleotide sequence may comprise a nucleotide sequence of prolactin (as shown in Table 1 below), which may further comprise a polyadenylation sequence.

The first nucleotide sequence may comprise that of a β-globin 5'-UTR coupled to a translation initiation sequence, particularly a Xenopus β-globin. The translation initiation sequence may comprise the Kozak consensus sequence A/GNNAUGN, preferably the consensus sequence ANNAUGG, preferably the consensus sequence which is ACCAUGG. The intiation sequence may further comprise a Shine-Dalgarno sequence.

The translation of the selected mRNA molecule may be effected herein in any prokaryotic or eukaryotic cell, which may be *E. coli* and the Eubacteria, Bacillus, Salmonella, Staphylococcus, Mycobacteria, Streptomyces, Archebacteria, yeast, fungi, mammalian cells, such as CHO, Vero cells, MDCK, human diploid cells, BHK and HeLa cells, oocytes, and plant cells.

In another aspect of the invention, there is provided a method of translating a selected mRNA molecule, which comprises:

coupling to a nucleic acid molecule transcribable to or which itself is an mRNA molecule at the 3'-end thereof a nucleotide sequence of the 3'-UTR of prolactin effective to increase the period of translation of said mRNA molecule in a cell, and effecting translation of said mRNA molecule in said cell.

The present invention further includes a hybrid nucleic acid molecule, comprising:

a first nucleotide sequence transcribable to or which is an mRNA molecule, a second nucleotide sequence operatively coupled to the 5'-end of said first nucleotide sequence and effective to increase the rate of translation initiation of the mRNA molecule in a cell, and a third nucleotide sequence operatively coupled to the 3'-end of said first nucleotide sequence and effective to increase the period of translation of said mRNA molecule in a cell.

The present invention may be employed to effect highly efficient translation of a wide variety of mRNA molecules, including mRNA molecules encoding a variety of proteins or peptides. Such encoded proteins or peptides may be selected from the group consisting of an enzyme, an antigen, an immunogen, an allergen, an enzyme inhibitor, a hormone, a lymphokine, an immunoglobulin or fragment thereof, a toxin, a toxin subunit, a mammalian protein, a structural protein, and a receptor.

Particular encoded proteins or peptides may include those selected from the group consisting of bovine preprolactin, human insulin receptor, α-subunit of the canine signal recognition particle receptor, the IgG binding domains of Staphylococcal protein A, HIV gag protein, CAT and HCV gB protein.

The present invention, therefore, provides a novel procedure for effecting translation of mRNA molecules in which an increased level of translation is achieved by employing a heterologous 3'-UTR.

BRIEF DESCRIPTION OF DRAWINGS

The present invention will be further understood from the following detailed description and Examples with reference to the accompanying drawings in which:

FIGS. 6 to 8 show urea-denatured gels of $^{35}$S labelled RNA after various time intervals of degradation.

FIG. 9 shows plasmid sequences used to transcribe the leaders employed herein. The SP6 promoter is marked with the thin line before the sequence. The initiation site is indicated with the thick underline. Relevant restriction sites are indicated.

IDENTIFICATION OF NUCLEOTIDE SEQUENCES

Figure 2:
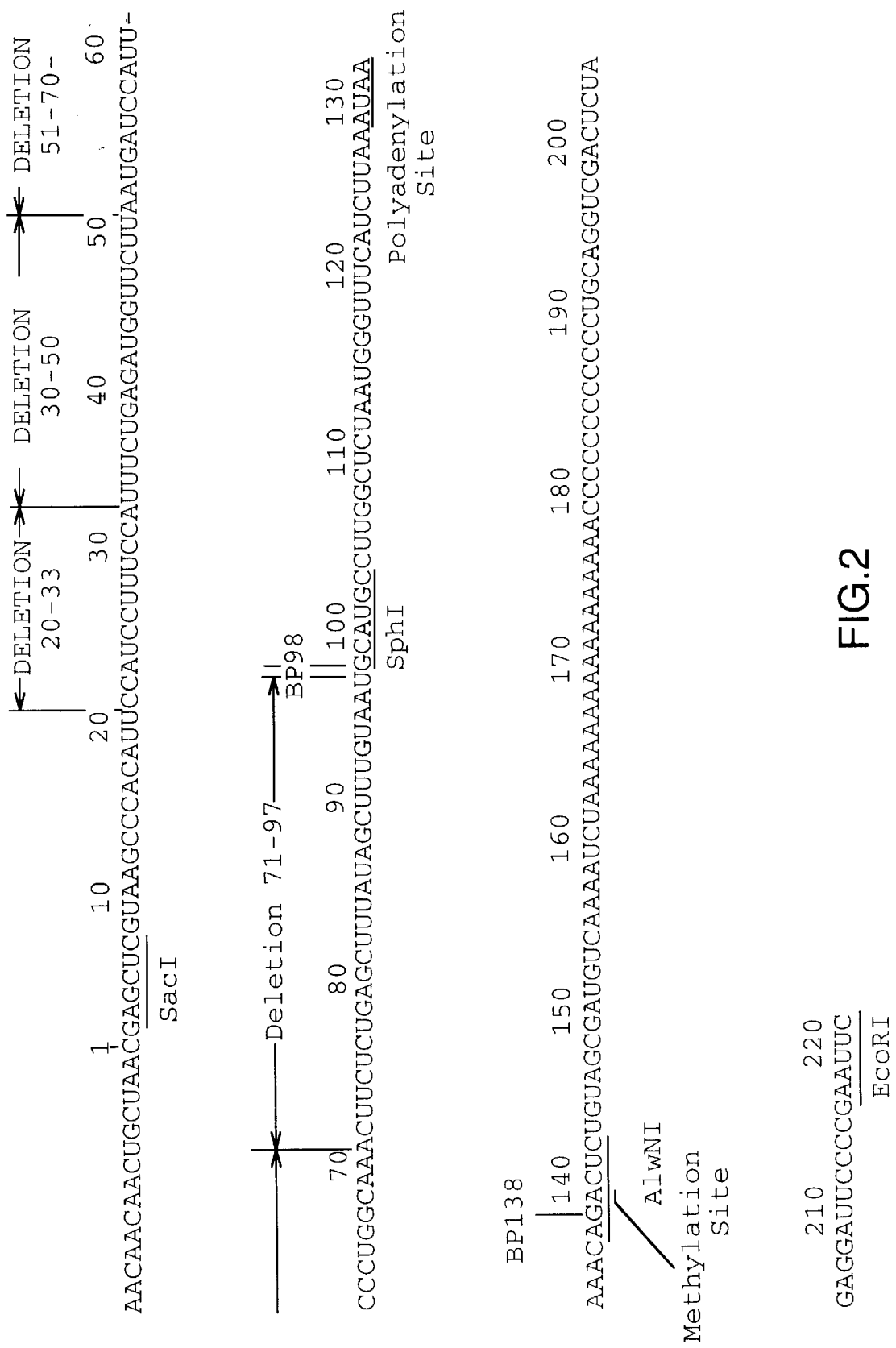
FIG. 2 shows the nucleotide sequence of the 3' UTR sequence of bovine preprolactin.

In the following Table I, the various SEQ ID NOs: are identified in relation to the nucleotide sequence as shown in FIG. 2 and the 5' leader, employed in FIG. 9.

TABLE I

| SEQ ID NO: | Fragment |
|---|---|
| 1 | whole length 3' UTR |
| 2 | nucleotides 1–161 of 3' UTR |
| 3 | nucleotides 51–97 of 3' UTR |
| 4 | nucleotides 1 to EcoRI site in polylinker |
| 5 | nucleotides 1–138 of 3' UTR |
| 6 | nucleotides 1–98 of 3' UTR |
| 7 | nucleotides 1–5 of 3' UTR |
| 8 | nucleotides 1–19 and 34–98 of 3' UTR |
| 9 | nucleotides 1–19 and 34–end of 3' UTR |
| 10 | nucleotides 1–33 and 51–98 of 3' UTR |
| 11 | nucleotides 1–33 and 51–end of 3' UTR |
| 12 | nucleotides 1–50 and 71–98 of 3' UTR |
| 13 | nucleotides 1–50 and 71–end of 3' UTR |
| 14 | nucleotides 1–70 of 3' UTR |
| 15 | nucleotides 1–70 and 98–end of 3' UTR |
| 16 | ATTTAGGTGACACTATAGAATACAAGCTCATGG |
| 17 | ATTTAGGTGACACTATAGAATACAAGCTGATCTACCATGG |
| 18 | ATTTAGGTGACACTATAGAATACAAGCTTG CTTGTTCTTTTTGCAGAAGCTCAGAATAAA CGCTCAACTTTGGCAGATCCATGG |
| 19 | ATTTAGGTGACACTATAGAATACAAGCTTG CTTGTTCTTTTTGCAGAAGCTCAGAATAAA CGCTCAACTTTGGCAGATCTACCATGG |

GENERAL DESCRIPTION OF THE INVENTION

Referring to FIG. 1, there is shown a comparison of the translation of the preprolactin deletion mutant Pt with different leader sequences in *Xenopus oocytes*. In vitro synthesized transcripts were normalized for RNA content by fluorometry, mixed with an equal volume of [$^{35}$S] methionine and injected into *Xenopus oocytes*. Oocytes were incubated for 4 hours in ND96 medium, homogenized and subjected to immunoprecipitation with anti-ovine prolactin antiserum (panel A). The products of the immunoprecipitation were separated by SDS-PAGE and fluorographed. The 5' untranslated region (5'UTR) is indicated below each lane and a summary of the leaders is shown in FIG. 9. SD leader is a standard plasmid sequence, as a negative control and not imparting any particular RNA translation stimulation. The KD leader contains the standard plasmid sequence and a Kozak consensus sequence (ACCAUGG SEQ ID NO: 20) as the initiation site. The insertion of this Kozak sequence increased, the rate of translation initiation as shown by the increased amount of Pt in lane 2. The leader UTR contains the Xenopus β-globin untranslated region and an unfavourable translation initiation site (CCCAUGG SEQ ID NO: 21). This leader resulted in a level of RNA translation approximately equivalent to the KD leader in lane 3. The leader UTK, contains the Xenopus β-globin untranslated region and an appropriately positioned Kozak consensus sequence as the initiation site. This semi-synthetic leader sequence is optimized for RNA translation as shown by the high level of translation Pt in lane 4. To further demonstrate the high level of translation efficiency imparted upon an mRNA by the inclusion of the Xenopus β-globin untranslated region and an appropriately positioned Kozak consensus sequence, these sequences were coupled to the 5' end of an mRNA encoding preprolactin and expressed from *Xenopus oocytes*. As shown in panel B of FIG. 1, prolactin continued to be synthesized and secreted into the medium for more than 60 hours post-injection. The level of prolactin secreted into the medium during a 24 hour period reached 125 ng per cell. At such a high level of expression, it was possible to detect the secretion of prolactin from *oocytes* by Coomassie blue staining of total culture medium after SDS-PAGE analysis. Typically the half-life for protein synthesis from an efficiently translated RNA after injection into *Xenopus oocytes* is a few hours (refs. 14, 23). In contrast, functional RNA encoding preprolactin persists for approximately 100 hours when the mRNA has the Xenopus β-globin untranslated region and an appropriately positioned Kozak consensus sequence coupled to the 5'-end thereof. Furthermore, since microinjected *oocytes* survive in culture for only 5–6 days it is possible that cell viability rather than RNA stability eventually limits the synthesis of preprolactin in these cells.

Figure 3:
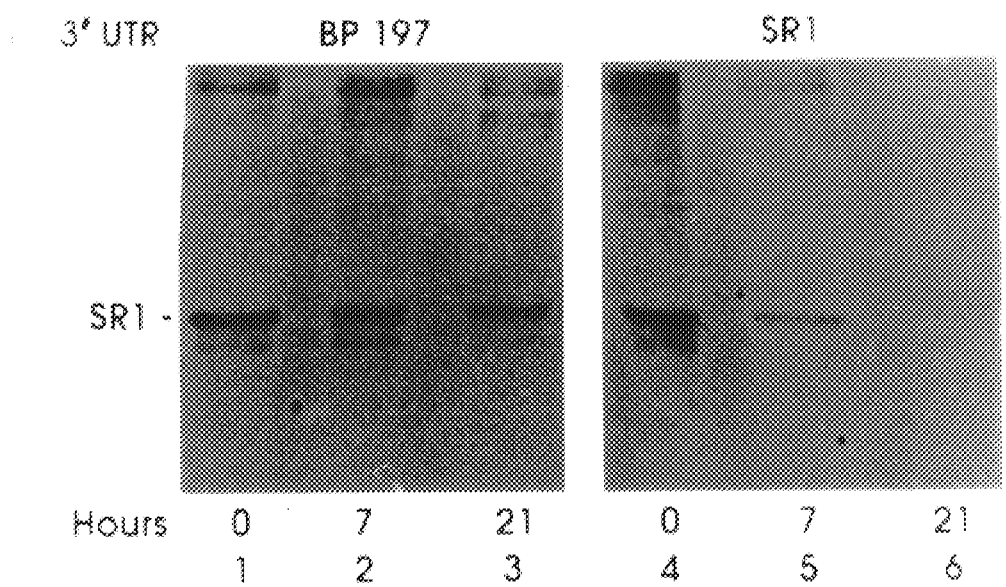
FIG. 3 comprising two panels labelled 3A and 3B, shows analysis by SDS-PAGE and fluorography of immunoprecipitated SR1 synthesized in *Xenopus* oocytes using SR1 and BP197 3'-UTR with the migration position of SR1 being to the left of the Figure.

To demonstrate that the preprolactin 3' UTR prolonged the translation of mRNAs encoding heterologous gene products, translation of RNAs encoding either a deletion mutant of the SRP receptor α-subunit termed SR1 or preproinsulin receptor was determined. The sequence bovine preprolactin gene is shown in FIG. 2 (SEQ ID NO: 2). Both coding regions were coupled at the 5'-end thereof to the UTK leader sequence and at the 3'-end thereof to the complete 197 nucleotide 3' UTR (BP197) (SEQ ID NO: 4). The SR1 3' UTR contains coding sequences as well as 406 nucleotides of the SRP receptor α-subunit 3' UTR. When the BP197 (SEQ ID NO: 4) sequence was fused to the SR1 coding sequence in place of this 3' UTR translation of the microinjected mRNA was extended by approximately 20 hours, (10 fold) FIG. 3, compare lanes 1–3 with 4–6.

The human insulin receptor has been expressed previously in *oocytes* but the level of expression was so low that it was only detectable on SDS-PAGE gels after in vitro labelling of the β-subunit with [γ-$^{32}$P]ATP (ref. 49). The expression of this molecule was increased by replacing the endogenous 5' leader with either the 5' UTK leader or the 5' UTK leader with added the BP197 3' UTR to the 3' UTR of the preproinsulin receptor sequence so that a composite 3' UTR (EBP) consisting of both the BP197 3' UTR and the 3' UTR of preproinsulin was produced.

Figure 4:
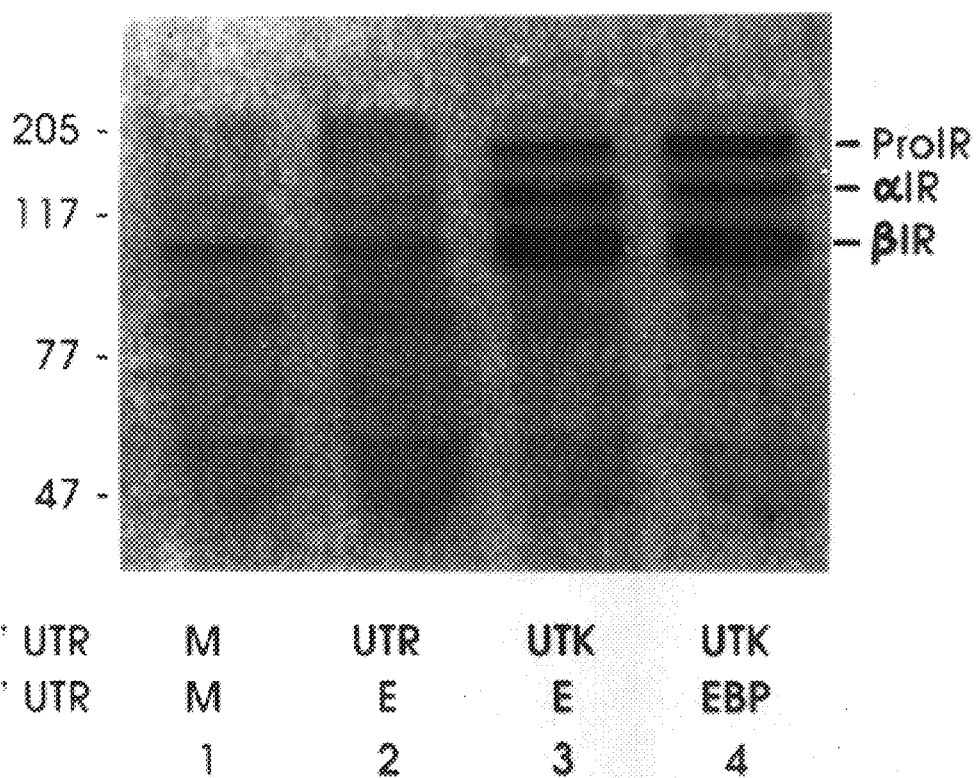
FIG. 4 shows analysis by SDS-PAGE and fluorography of immunoprecipitated insulin receptor synthesized by *Xenopus oocytes*. The migration position of the proreceptor, α-subunit and β-subunit of the insulin receptor are indicated to the right of the Figure. The migration positions of molecular weight markers (in kDa) are indicated at the left of the Figure.

Thus, referring to FIG. 4, there is illustrated the effect of these 5' UTR replacements and 3' UTR additions to the translation of insulin receptor mRNA in *Xenopus oocytes*. *Oocytes* were injected with 50 nl/*oocyte* in vitro synthesized transcript, and incubated in 1 mCi [$^{35}$S] methionine/10 ml ND96 for 24 hours. The medium was replaced with fresh medium and incubation continued for another 16 hours. Immunoprecipitated insulin receptor translation products were analyzed for sets of 6 *oocytes* by SDS-PAGE and fluorography. Lane 1 shows, control *oocytes* mock-injected with water. The 3' untranslated regions are indicated as: E, endogenous 3' UTR; EBP, fusion of the endogenous and BP197 3' UTRs. The UTR and UTK 5' leader sequences are defined above. The migration positions of the proreceptor, α-subunit and β-subunit of the insulin receptor are indicated to the right of FIG. 4. The migration positions of molecular weight markers (in kDa) are indicated at the left of FIG. 4.

In continuously labelled cells addition of the UTK leader dramatically improved the synthesis of the insulin receptor. As a result the early translation product (proreceptor) and the processed α and β subunits are easily detected by immunoprecipitation of homogenates prepared from microinjected *oocytes* (FIG. 4 compare lanes 2 and 3). Although addition of the BP197 3' UTR did not significantly change the amount of the processed subunits observed, the amount of proreceptor detected 40 hours post-injection was increased by 3 fold (FIG. 4 compare the top bands in lanes 3 and 4). This increase in proreceptor synthesis indicates that the mRNA encoding preproinsulin receptor is translated for a longer time when the BP197 3' UTR is coupled thereto.

To particularly localize the sequences within the BP197 3' UTR (SEQ ID NO: 4) responsible for increasing the period of translation of an mRNA molecule coupled thereto a series of mutants containing progressive deletions was constructed and analyzed. The plasmid encoding Pt with the UTK leader and BP197 3' UTR was used for these experiments as Pt is not secreted from *oocytes* thereby simplifying the measurement of protein synthesis at different time points. This plasmid was digested with restriction enzymes that cut the plasmid within the 3' UTR at the positions indicated in FIG. 2 and transcript was synthesized in vitro and injected into *oocytes*. At different times after injection *oocytes* were pulse labelled with [$^{35}$S] methionine for 4–5 hours. The relatively long pulse time ensured that the label completely equilibrated within the cell (ref. 41).

Figure 5:
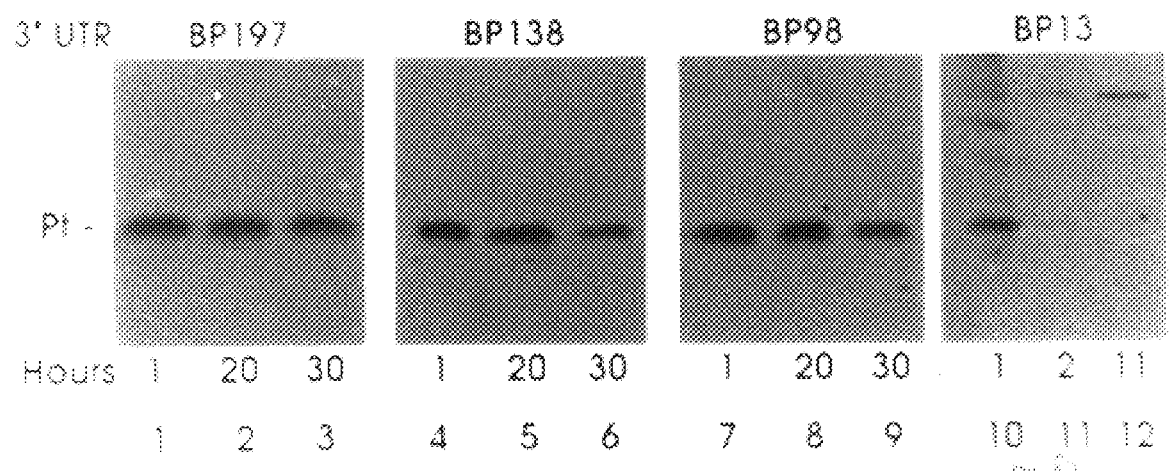
FIG. 5 comprising four panels labeled 5A, 5B, 5C and 5D, shows analysis by SDS-PAGE and fluorography of immunoprecipitated Pt synthesized from transcripts containing truncated 3'-UTRs as indicated above the panels. The migration position of Pt is indicated to the left of the Figure.

Referring to FIG. 5, there is illustrated the truncation of such mRNAs having 3' UTR. The transactions are as follows:

| | Nucleotides in 3' UTR | SEQ ID NO: |
|---|---|---|
| B197 | No truncation | 4 |
| BP138 | 1–138 | 5 |
| BP98 | 1–98 | 6 |
| BP13 | 1–5 | 7 |

Normalized transcript was injected into cells and then at the time point indicated below each lane a set of 5 *oocytes* was placed in media containing [$^{35}$S] methionine (0.5 mCi/10 ml) and labelled for 5 hours. After labelling, *oocytes* were homogenized and translation products were immunoprecipitated with anti-ovine prolactin antiserum and separated by SDS-PAGE. The gels were fluorographed, dried and exposed to film. The migration position of Pt is indicated to the left of FIG. 5.

Comparison of the amount of Pt synthesis 30 hours after RNA injection revealed that deletion of the 3' end of the sequence (to produce BP138) (SEQ ID NO: 5) reduced the translational half-life of the injected RNA somewhat (FIG. 5 lanes 3, 6, 9). In this experiment the half-lives for translation of the RNA with the BP138 and BP98 3' UTRs were both approximately 30 hours. In contrast, only about 20% of the RNA with the BP197 3' UTR was inactive 30 hours post-injection.

Molecules with the BP98 3' UTR do not contain the poly A sequence, methylation site or a polyadenylation signal yet the RNA was remarkably stable (measured translational half-life about 30 hours). Translation of molecules with the BP13 3' UTR could not be detected in *oocytes* 2 hours post-injection (FIG. 5, lane 11). The construct containing the BP13 3' UTR ends with an EcoRI restriction site therefore, the last 5 bases in the UTR are identical to the last five bases of BP197.

To further localize the sequence within the BP197 3' UTR (SEQ ID NO: 4) further deletions from the 3' UTR# were made as shown in FIG. 2.

The translation promotion demonstrated in *oocytes* was reflected by greater mRNA stability in vitro RNA degradation system, which directly measures the mRNA stability. The truncations made as follows:

| | Nucleotides in 3' UTR | SEQ ID NO: |
|---|---|---|
| Sac I | 1–5 | 7 |
| Sph I | 1–98 | 6 |
| EcoRI | No truncation | 4 |
| SphI/ deletion 20–33 | 1–19; 34–98 | 8 |
| EcoRI/ deletion 20–33 | 1–19; 34–end of 3' UTR | 9 |
| SphI/ deletion 34–50 | 1–33; 51–98 | 10 |
| EcoRI/ deletion 34–50 | 1–33; 51–end of 3' UTR | 11 |
| SphI/ deletion 51–70 | 1–50; 71–98 | 12 |
| EcoRI/ deletion 51–70 | 1–50; 71–end of 3' UTR | 13 |
| SphI/ deletion 71–97 | 1–70; | 14 |
| EcoRI/ deletion 71–97 | 1–70; 98–end of 3' UTR | 15 |

Referring to FIGS. 6, 7 and 8 there is illustrated the stability of such truncated mRNAs by a degradation assay.

RNA was produced by in vitro transcription using SP6 RNA polymerase. Radiolabelling of the RNA was achieved by including $^{35}$S-UTP at a concentration of 100 nM in the transcription mix.

The degradation assay is based upon a Rabbit Reticulocyte Lysate preparation. The preparation is not subjected to nuclease or gel-filtration treatment. Radiolabelled RNA was incubated in a buffered mixture containing lysate, Creatine Kinase and 'E-mix' (containing all 20 amino acids, Creatine Phosphatase, ATP and GTP). The degradation assay was stopped at time points following the start of the reaction by the addition of Vanadyl Ribonucleoside Complexes, and then snap-frozen in liquid nitrogen. RNA was recovered by Phenol/Chloroform extraction followed by ethanol precipitation. Resuspended RNA was then analyzed on a TBE/urea denaturing acrylamide gel, which was then dried and exposed to autoradiography film.

FIG. 6 shows the effect of incubating radiolabelled RNA, synthesized from SacI (SEQ ID NO: 7), SphI (SEQ ID NO: 8) or EcoRI (SEQ ID NO: 4) truncated plasmids, in the degradation assay for 0, 30, 60 or 120 min. In keeping with the data obtained for the *Xenopus oocytes*, it can be seen that the SacI product is unstable, decaying such that it has disappeared after 60 min. The SphI product is more stable, decaying after 120 min. The EcoRI product, however, is still stable after 120 min.

FIGS. 7 and 8 show the degradation patterns of the RNA's created by further deletions. Deletions of the nucleotides between positions 20–33 and 34–50 produce essentially the same pattern as seen for wild type. Deletions between nucleotides 51–70 and 71–97 causes no difference in stability when the DNA template is truncated at the SphI site. However, the transcript produced when the template is truncated at EcoRI is much less stable in both cases than is wild type. Thus, there are nucleotides between positions 51 and 97 which contribute to the stability of the mRNA molecule.

EXAMPLES

The above disclosure generally describes the present invention. A more complete understanding can be obtained by reference to the following specific Examples. These Examples are described solely for the purposes of illustration and are not intended to limit the scope of the invention.

Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply within the ability of those skilled in the art.

Example 1

This Example describes construction of certain plasmids.

A plasmid encoding the α-subunit of SRP receptor was modified by introducing a termination codon (in an XbaI linker) into the coding region at codon 426. The plasmid was then cut with XbaI, and repaired with the Klenow fragment of polymerase and a SacI linker was added. These manipulations resulted in a plasmid encoding the deletion mutant SR1, containing the first 426 amino acids of SRP receptor α-subunit with a SacI site immediately following the termination codon. Thus, the SR1 3' UTR contains 636 nucleotides of coding sequence and 406 nucleotides of the SRP receptor α-subunit 3' UTR. The insulin receptor plasmid contains 180 nucleotides of the endogenous 3' UTR ending with an SpeI restriction site. For cloning purposes the plasmid was cut with SpeI, end repaired using the Klenow fragment of DNA polymerase and a SacI linker was inserted.

Construction of plasmids encoding either preprolactin or the preprolactin deletion mutant Pt with the SD, KD, UTR and UTK leaders were described previously (ref. 38). Sequences for these leaders (SEQ ID NOS: 16–19) are shown in FIG. 9. The complete 3' UTR and coding region of Pt is similar to that of preprolactin, except that amino acids 2 to 58 of the mature prolactin domain have been deleted. In addition, a SacI restriction site was introduced immediately following the termination codon of Pt using the naturally occurring EspI site overlapping the termination codon. The translation start site in the UTK leader is contained within an NcoI site as seen in FIG. 9. By first removing the SacI site in the polylinker sequence at the 3' end of the Pt construct, it was possible to replace the Pt coding region in this plasmid with other coding sequences by digestion with NcoI and SacI. The resulting plasmids contained the desired coding region flanked with the UTK leader and the bovine preprolactin 3' UTR. Plasmids containing the insulin receptor and SRI coding regions were assembled in this way. To construct plasmids with the UTK leader and the endogenous 3' UTR use was made of a plasmid (pSPUTK, available from Stratagene) containing the UTK leader followed by a multiple cloning site. The 3' and 5' ends of the constructs were sequenced using the NEB vent polymerase sequencing system according to the manufacturers instructions.

Example 2

This Example describes transcription of mRNA in vitro.

Plasmids prepared as described in Example 1 were linearized by digestion with a suitable restriction enzyme before transcription in vitro (ref. 39). In most cases, an EcoRI restriction site within the polylinker at the 3' end of the 3' UTR was used for linearization. Restriction sites within the preprolactin 3' UTR were used to produce transcripts truncated at different positions within the 3' UTR. Because SphI and AlwNI leave 3' overhangs, the DNA was end repaired using the Klenow fragment of DNA polymerase prior to transcription in vitro (ref. 39). Sp6 polymerase reactions generating capped transcripts were as described previously except that glutathione buffer (50 mM reduced glutathione, 10 mM oxidized glutathione and 20 mM Hepes pH 7.5) was used in place of DTT (ref. 40). Transcripts were normalized for RNA contents using a fluorometric assay described previously (ref. 33). An aliquot of each transcript was translated in a reticulocyte lysate reaction prior to injection to ensure that full length molecules were synthesized from the RNA. Reticulocyte lysate translations were effected as described previously (ref. 38) and contained 1 µl of the transcription reaction and 10 µCi [$^{35}$S] methionine.

Example 3

This Example illustrates translation of mRNA in *Xenopus* oocytes.

Adult female breeding *Xenopus laevis* were purchased from Boreal (St. Catharines, Canada). Ovarian fragments were surgically removed from anaesthetized animals, stage VI *oocytes* were manually dissected and stored at 19° C. in ND96 media (96 mM NaCl, 2 mM KCl, 1 mM MgCl 1 mM CaCl 5 mM Hepes, pH 7.6) supplemented with antibiotics. *Oocytes* were injected using a model NA-1, injection system (Sutter Instrument Co. Novato, Calif.). Borosilicate micropipettes (I.D. 0.5 mm, O.D. 1.0 mm) were pulled using a K. T. Brown Type Puller and bevelled using a model BV-10 beveller (both Sutter Instrument Co. Novato, Calif.).

Translational efficiency in *Xenopus oocytes* was determined by co-injection of in vitro synthesized transcription products and [$^{35}$S] methionine. Normalized SP6 transcription products were mixed with an equal volume of [$^{35}$S] methionine (10 mCi/ml) and 50 nl were injected into each *oocyte*. Groups of 40 to 50 *oocytes* were injected with each transcript and incubated in ND96, for the time indicated. To assess the period of translational activity of the injected RNA, transcript was injected alone and cells were pulse labelled at the indicated times by placing 5 to 10 *oocytes* in 0.5 ml ND96 containing [$^{35}$S] methionine (0.05 mCi/ml) for 4 or 6 hours for Pt and SR1 transcripts respectively. To follow insulin receptor expression. [$^{35}$S] methionine was present during the entire 40 hour incubation.

After incubation, *oocytes* were homogenized and the labelled proteins were recovered by immunoprecipitation as described (ref. 27) except for SR1 translation products where the solubilization and initial wash buffer contained 1.5% Triton X-100, 500 mM NaCl, 100 mM Tris-Cl pH 8.0, 10 mM EDTA, the mouse IgG1 monoclonal antibody (ref. 42) was precipitated using an equal mixture of protein A and protein G agarose, and the initial pelleting step was over a 0.5M sucrose cushion. Antibodies to ovine prolactin and human insulin receptor (AB-1) were obtained from United States Biochemicals (Cleveland, Ohio), and Oncogene Science, (Uniondale, N.Y.) respectively. Protein A coupled to agarose was purchased from BioRad Laboratories (Mississauga, Canada) and protein G coupled to agarose from Oncogene Science (Uniondale, N.Y.).

Figures 1A, 1B:
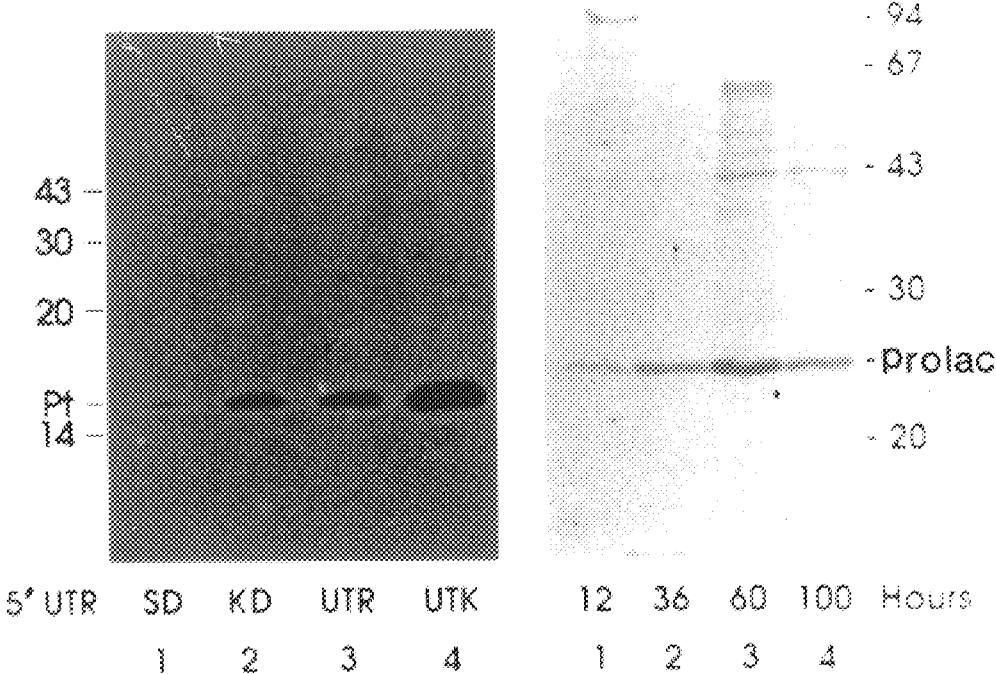
FIG. 1A shows analysis by SDS-PAGE and fluorography of immunoprecipitated Pt synthesized in injected *Xenopus* oocytes, with the migration positions of Pt and molecular weight markers indicated to the left of the panel.
FIG. 1B shows visualization of prolactin secreted by *Xenopus* oocytes by Coomassie blue staining.

Immunoprecipitation products were separated by SDS-PAGE using the Tris-tricine buffer system, fluorographed and exposed to film (ref. 43). Relative protein synthesis was quantified by densitometer. The results obtained are shown in FIG. 1A.

Example 4

This Example contains a discussion of the level of mRNA translation.

Previously there was reported that the UTK leader increased the rate of translation initiation for a variety of coding regions in vitro (ref. 38). The previous in vitro results have been extended to an in vivo whole cell system. To this end, transcription products from SP6 polymerase reactions were injected into *Xenopus oocytes* and protein synthesis was examined by immunoprecipitation of the prolactin deletion mutant Pt, from cells labelled with $^{35}$S methionine as described in Example 3. The 5' leader sequences used were the same as examined previously (ref. 38) and were selected to permit comparison of the effect on translation of the UTR sequence with that of the consensus sequence for translation initiation (ref. 44). The SD and KD leaders contain plasmid derived sequence between the SP6 promoter and the translation start site and therefore are typical of the untranslated sequences obtained using most standard cloning vectors. The translation start sites for the SD and KD leaders are the relatively unfavourable initiation sequence CCCVAGG (SEQ ID NO: 21) and the strong initiation sequence ACCAUGG (SEQ ID NO: 20) respectively (ref. 45). The UTR and UTK leaders contain the Xenopus β-globin 5' UTR linked to these compromised and strong initiation sequences respectively.

To assay the translational efficiency of the different leaders in a whole-cell system, transcription products were injected into *Xenopus oocytes*, as described in Example 3. Microinjection permits direct comparison of different RNA's translation independent of transcription. In addition, the differences observed are unlikely to be influenced by rates of maturation of transport from the nucleus because the RNA is injected directly into the cytoplasm. Microinjection of RNA containing the UTK leader into *oocytes* resulted in more synthesis of Pt during a four hour pulse label than was obtained for RNA with the other leaders, FIG. 1A. Moreover, both the UTR and the consensus sequence for translation initiation contributed to the increase in protein synthesis observed (FIG. 1A compare lanes 2 and 3 with 4). Densiometry for five separate experiments indicated that the increase in translation efficiency due to addition of the consensus initiation sequence was approximately the same as that due to the UTR sequence (3 to 4 fold). The net increase due to the two sequences together was greater than 7 fold indicating that the two sequences independently promote efficient translation.

The observation that regions in the 5' UTR increase translation efficiency independently from the consensus sequence for efficient initiation, (FIG. 1A) is not predicted by the scanning model for initiation (ref. 46). The scanning model states that the nucleotide sequence immediately surrounding the initiator AUG is the primary determinant of translational efficiency and does not allow for regions of the 5' UTR being involved in enhancing translation (ref. 33). However, the Xenopus 5' UTR clearly increased translational efficiency even for mRNAs with a compromised initiation sequence in diverse systems and *Xenopus oocytes* indicating that this region acts as a general enhancer of eukaryotic translation.

After microinjection of preprolactin RNA containing the UTK leader into *Xenopus oocytes*, the amount of protein secreted into the medium during a 24 hour period was as high as 125 ng per cell. Therefore, it was possible to detect the secretion of prolactin from *oocytes* by Coomassie blue staining of total culture medium after SDS-PAGE, as seen in FIG. 1B. Most of the preprolactin labelled in a 4 hour pulse was secreted as prolactin from the *oocytes* within 6 hours (ref. 27). It is surprising that prolactin secretion could be detected by Coomassie blue staining of total *oocyte* media up to 6 days following infection of the RNA (FIG. 1B). Typically the half-life for protein synthesis from an efficiently translated RNA after injection into *Xenopus oocytes* is a few hours (refs. 15, 16). In contrast, densitometry of the data obtained from three independent experiments similar to that shown in FIG. 1B revealed that functional RNA encoding preprolactin persists for at least 100 hours. Because microinjected *oocytes* survive in culture for only 5 to 6 days it is possible that cell viability rather than RNA stability eventually limits the synthesis of preprolactin in these cells.

The functional half-life of a coding region is often determined by sequences within the 3' UTR (refs. 13, 17). The nucleotide sequence and other salient features deduced from the DNA sequence of the prolactin 3' UTR are shown in FIG. 2 (SEQ ID NO: 1). DNA sequencing of this region revealed that the poly A sequence is followed by a run of 10 C's. Although this sequence is not part of the authentic preprolactin 3' UTR as it was added during the initial cDNA cloning of preprolactin, it was part of the 3' UTR assayed above, and was therefore included in the constructs described herein. The preprolactin 3' UTR contains a nuclear polyadenylation sequence but lacks the cytoplasmic polyadenylation element necessary for addition of A residues in the cytoplasm of *Xenopus oocytes* (ref. 47). Other previously characterized motifs such as the AU-rich motif known to destabilize a wide variety of mRNAs (ref. 19) are absent from the preprolactin 3' UTR. However, the sequence does contain 4 repeats of the sequence CCAU.

Example 5

This Example illustrates the use of preprolactin 3' UTR to prolong translation of heterologous mRNA.

Protein synthesis was measured for hybrid RNAs encoding either a deletion mutant of the SRP receptor α-subunit termed SR1 or preproinsulin receptor. Both coding regions were flanked by the UTK leader sequence and the complete 3' UTR (BP197-SEQ ID NO: 4). The SR1 3' UTR contains coding sequences as well as 406 nucleotides of the SRP receptor α-subunit 3' UTR. When the BP197 sequence was fused to the SR1 coding sequence in place of this 3' UTR translation of the microinjected RNA was extended by approximately 20 hours, (10 fold), as seen in FIG. 3, compare lanes 1 to 3 with 4 to 6. Although the SR1 3' UTR contains coding sequences, the period during which the injected RNA is translated (FIG. 3, lanes 4 to 6) is similar to that of other injected RNAs. The apparent stability of the hybrid RNA is due to prolonged translation of the species with the BP197 3' UTR rather than rapid degradation of the RNA with the SR1 3' UTR.

The human insulin receptor has been expressed previously in *oocytes* but was only detectable on SDS-PAGE gels after in vitro labelling of the β-subunit with [γ-$^{32}$P]ATP (ref. 26). To improve expression of the human insulin receptor, the endogenous 5' leader was replaced with the UTK leader and the BP197 3' UTR was added to the 3' UTR of the preproinsulin receptor sequence. In continuously labelled cells, addition of the UTK leader dramatically improved the synthesis of the insulin receptor. As a result, the early translation product (proreceptor) and the processed α and β subunits are easily detected by immunoprecipitation of homogenates prepared from microinjected *oocytes* (as seen in FIG. 4, compare lanes 2 and 3). Although addition of the BP197 3' UTR did not significantly change the amount of the processed subunits observed, the amount of proreceptor detected 40 hours post injection was increased by 3 fold (see FIG. 4, compare the top bands in lanes 3 and 4). The increase in proreceptor synthesis results from the mRNA encoding preproinsulin receptor being translated for a longer time when fused to the BP197 3' UTR.

Example 6

This Example illustrates the effect of modifications to the preprolactin 3' UTR on mRNA translation.

A series of mutants containing deletions from BP197 3' UTR were examined (SEQ ID NOs: 5–7 for these mutations identified in Table 1 above). The plasmid encoding Pt with the UTK leader and BP197 3' UTR was used for these experiments as Pt is not secreted from oocytes, thereby simplifying the measurement of protein synthesis at different time points. This plasmid was digested with restriction enzymes that cut the plasmid within the 3' UTR at the positions indicated in FIG. 2, the transcript was synthesized in vitro and injected into *oocytes*. At different times after injection, *oocytes* were pulse labelled with [$^{35}$S] methionine for 4 to 5 hours. The relatively long pulse time ensured that the label completely equilibrated within the cell (ref. 16).

Comparison of the amount of Pt synthesis 30 hours after RNA injection revealed that deletion of the 3' end of the sequence reduced the translational half-life of the injected RNA somewhat (see FIG. 5, lanes 3, 6, 9). In this experiment, the half-lives for translation of the RNA with the BP138 and BP98 3' UTRs were both approximately 30 hours. In contrast, only about 20% of the RNA with the BP197 3' UTR was inactive 30 hours post-injection. The additional sequences within the BP197 3' UTR included a sequence of 17 A's followed by 10 C's and the predominant site of methylation in vivo (ref. 48). Based on previous observations that a poly A tail containing 32 A's but not 17 A's was sufficient for mRNA stability it is unlikely that the poly A sequence contributes significantly to RNA stabilization (ref. 18).

Molecules with the BP98 3' UTR do not contain the poly A sequence, methylation site or a polyadenylation signal, yet the RNA was remarkably stable (measured translational half-life 30 hours). In contrast, other RNAs microinjected into *Xenopus oocytes* are found only in non-polycomal fractions within 4 hours of deadenylation (ref. 47). Consistent with these results translation of molecules with the BP13 3' UTR could not be detected in *oocytes* 2 hours post-injection (see FIG. 5, lane 11). The construct containing the BP13 3' UTR ends with an EcoRI restriction site, therefore, the last 5 bases in the UTR are identical to the last five bases of BP197. RNA from another plasmid containing a 38 nucleotide 3' UTR between the stop codon and an EcoRI linearization site was also translated for less than 2 hours indicating that the short length of the BP13 3' UTR does not account for the differences observed in FIG. 5. Taken together, these results indicate that there is a sequence within the first 98 bases of the BP197 3' UTR that prolongs translation of RNAs in *Xenopus oocytes*.

Example 7

This Example describes a degradation assay for determining the stability of mRNAs.

Radioactive RNA was prepared as follows:

Plasmid DNA was linearized with an appropriate restriction enzyme. The enzyme was then heat killed at 70° C. for 20 min. Where necessary, the DNA was treated with Klenow Fragment. Proteins were removed by phenol/chloroform extraction, the DNA was precipitated with ethanol and then resuspended in TE buffer. For transcription, 1 µl (approx. 1 µg) of linearized DNA is incubated with:

2 µl CB5X
2 µl NTP mix
1 µl $^{35}$S-UTP

1 µl DTT
0.2 µl tRNA
0.4 µl RNAguard
0.4 µl SP6 RNA polymerase (10 U µl$^{-1}$)
2 µl MQ Water
for 1h at 37° C.

Degradation assay

Radioactive RNA was incubated in a degradation assay mix at 24° C. for varying lengths of times. The degradation assay was set up as follows:

0.5 µl CB20X (linked)
4.2 µl Rabbit Reticulocyte Lysate
2.0 µl "E-mix"
0.1 µl Creatine Kinase (4 mg ml$^{-1}$)
1.0 µl radioactive RNA
2.2 µl MQ Water Degradation was halted by the addition of 2 ul 200 mM Ribonucleoside-Vanadyl Complex (NEB), and then snap-frozen in liquid nitrogen.

RNA was recovered from the mix by phenol/chloroform extraction and ethanol precipitation. Precipitated nucleic acids was resuspended in 3 µl of TE buffer. Formamide denaturing loading buffer was added to 9 µl total, and the sample was heated at 70° C. for 10 min. Of the sample, 6 µl were analyzed on a TBE/urea acrylamide gel. Following the run, the gel was dried and exposed to autoradiographic film.

The various buffers used in this assay were prepared as follows:

|  | RRL | | WG | |
|---|---|---|---|---|
| CB5X | vol | final [ ] | vol | final [ ] |
| 1M HEPES-K pH 7.5 | 400 µL | 80 mM | 400 µL | 80 mM |
| 1M MgCl$_2$ | 75 µL | 15 mM | | |
| 1M MgAc$_2$ | | | 70 µL | 14 mM |
| 0.1M spermidine | 100 µL | 2 mM | 100 µL | 2 mM |
| water | 425 µL | | 430 µL | |
| total | 1 mL | | 1 mL | |
| 4 NTP (5X) | uncapped | | capped | |
| 0.1M ATP | 150 µL | | 150 µL | |
| 0.1M CTP | 150 | | 150 | |
| 0.1M UTP | 150 | | 150 | |
| 0.1M GTP | 150 | | 15 | |
| water | 400 | | 535 | |
| total | 1 mL | | 1 mL | | adjust pH to 7.0 with 2M Tris base.

SUMMARY OF THE DISCLOSURE

In summary of this disclosure, the present invention provides a novel method of promoting translation of an mRNA molecule in a cell using nucleotide sequences provided at 5' and 3' ends of itself or the mRNA molecule itself a nucleic acid molecule transcribable to the mRNA molecule, so as to increase the rate of translation initiation of the mRNA molecule and to increase the period of translation thereof. Modifications are possible within the scope of this invention.

REFERENCES

1. Cigan, A. M., and T. F. Donahue. (1987) Gene 59, 1–18.
2. Kozak, M. (1988) J. Cell Biol. 107, 1–7.
3. Lodish, H. F. (1976) Ann. Rev. Biochem. 45, 39–72.
4. Liebhaber, S. A., F. Cash and S. S. Eshleman. (1992) Journal of Molecular Biology 226, 609–621.
5. Sorenson, M. A., C. G. Kurland and S. Pedersen. (1989) J. Mol. Biol. 207, 365–377.
6. Sharp, P. M., and K. M. Devine. (1989) Nucleic Acids Res. 17, 5029–5039.
7. Baim, S. B. and F. Sherman. (1988) Mol. Cell. Biol. 8, 1591–1601.
8. Doohan, J. P. and C. E. Samuel. (1992) Virology 186, 409–425.
9. Kim, J., P. G. Klein and J. E. Mullet. (1991) J. Biol. Chem. 266, 14931–14938.
10. Kim, J., M. J. Hollingsworth. (1992) Anal. Biochem. 206, 183–188.
11. Rabinovich, Y. M. and M. O. Kreinin. (1991) Biochimica et Biophysica Acta 1089, 193–196.
12. Young, J. H. C., A. Vassilakos and D. W. Andrews, submitted.
13. Saini, K. S., I. C. Summerhayes and P. Thomas (1990) Mol. Cell. Biochem. 96, 15–23.
14. Jackson, R. J. (1993) Cell 74, 9–14.
15. Drummond, D. R., J. Armstrong and A. Colman. (1985) Nucleic Acids Res. 13, 7375–7394.
16. Nudel, U., H. Soreq and U. Z. Littauer. (1976) Eur. J. Biochem. 64, 115–121.
17. Bernstein, P. and J. Ross. (1989) TIBS 14, 373–377.
18. Galili, G., E. E. Kawata, L. D. Smith and B. A. Larkins (1988) J. Biol. Chem. 263, 5764–5770.
19. Jackson, R. J. and N. Standart. (1990) Cell 62, 15–24.
20. Wickens, M. (1990) TIBS 15, 320–324.
21. Laird-Offringa, I. A., C. A. dewit, P. Elfferich and A. J. van der Eb. (1990) Mol. Cell. Biol. 10, 6132–6140.
22. Aharon, T., and R. J. Schneider. (1993) Mol. Cell. Biol. 13, 1971–1980.
23. Ratnasabapathy, R., S. L. Hwang and D. L. Williams. (1990) J. Biol. Chem. 265, 14050–14055.
24. Saini, K. S. and I. C. Summerhayes. (1991) Biochem. Cell. Biol. 69, 415–417.
25. Brawerman, G. (1989) Cell 57, 9–10.
26. Pelham, H. R. B. (1978) Eur. J. Biochem. 85, 457–462.
27. Pelletier, J. and N. Sonenberg. (1988) Nature 334, 320–325.
28. Jobling, S. A. and L. Gehrke. (1987) Nature 325, 622625.
29. Jobling, S. A., C. M. Cuthbert, S. G. Rogers, R. T. Fraley and L. Gehre. (1988) Nucleic Acids Res. 16, 4483–4498.
30. Johansen, H., D. Schumperli and M. Rosenberg. (1984) Proc. Natl. Acad. Sci. USA 81, 7698–7702.
31. Elroy-Stein, O., T. R. Fuerst and B. Moss. (1989) Proc. Natl. Acad. Sci. USA 86, 6126–6130.
32. Gallie, D. R., D. E. Sleat, J. W. Watts, P. C. Turner and T. M. A. Wilson. (1987) Nucleic Acids Res. 15, 3257–3273.
33. Gallie, D. R., D. E. Sleat, J. W. Watts, P. C. Turner and T. M. A. Wilson. (1987) Nucleic Acids Res. 15, 8693–8711.
34. Berkner, K. L. and P. A. Sharp. (1985) Nucleic Acids Res. 13, 841–856.
35. Curran, J. and D. Kolakofsky. (1989) EMBO J. 8, 521526.
36. Lazarus, P. (1992) Oncogene 7, 1037–1041.
37. Tyc, K., M. Konarska, H. J. Gross and W. Filipowicz. (1984) FEBS 140, 503–511.
38. Falcone, M. and D. W. Andrews. (1991) Mol. Cell. Biol. 11, 2656–2664.
39. Andrews, M. T. (1989) Promega Notes No. 17:1.
40. Gurevich, V. V., I. D. Pokrovskaya, T. A. Obukhova and S. A. Zozulya. (199_) Anal. Biochem. 195, 207–213.

41. Simon, K., E. Perara and V. R. Lingappa. (1987) J. Cell Biol. 104: 1165–1172.
42. Tajima, S., L. Lauffer, V. L. Rath and P. Walter. (1986) J. Cell Biol. 103, 1167–1178.
43. Schagger, H. and G. von Jagow. (1987) Anal. Biochem. 166, 368–379.
44. Kozak, M. (1978) Cell 44, 283–292.
45. Kozak, M. (1987) Nucleic Acids Res. 15, 8125–8148.
46. Kozak, M. (1989) J. Cell Biol. 108, 229–241.
47. Fox, C. A. and M. Wickens. Genes Dev. 4, 2287–2298.
48. Narayan, P., Ludwiczak, R. L., Goodwin, E. C. and Rottman, F. M. (1994) Nucleic Acids Res. 22, 419–426.
49. Vera, J. C. and O. M. Rosen. (1990) Mol. Cell. Biol. 10, 743–751.

---

What we claim is:

1. A method of translating a selected mRNA molecule to provide an increased level of translation thereof, which comprises:

coupling to a nucleic acid molecule transcribable to or which itself is an mRNA molecule at the 5'-end thereof a first nucleotide sequence heterologous to the nucleic acid molecule comprising a Xenopus β-globin 5'-untranslated region (UTR) coupled to a translation initiation sequence for said nucleic acid molecule comprising a Kozak consensus ANNAUGG and effective to increase the rate of translation initiation of said mRNA molecule in a cell, coupling to said nucleic acid molecule at the 3'-end thereof a second nucleotide sequence heterologous to the nucleic acid molecule, comprising at least a portion of a 3'-untranslated region (UTR) of a prolactin gene shown in FIG. 2 and selected from the group consisting of nucleotide sequences having SEQ ID NOS: 1, 3, 8, 9, 10, 11, 12 and 14 in Table I and effective to increase the period of translation of said mRNA molecule in a cell, and effecting translation of said mRNA molecule in said cell.

2. The method of claim 1 including coupling a polyadenylation sequence to the 3'-end of said second nucleotide sequence prior to said translation step.

3. The method of claim 1 wherein said consensus sequence is ACCAUGG.

4. The method of claim 1 wherein said initiation sequence further comprises a Shine-Dalgarno sequence.

5. The method of claim 1 wherein said cell is a prokaryotic or a eukaryotic cell.

6. A method of translating a selected mRNA molecule, which comprises:

coupling to a nucleic acid molecule transcribable to or which itself is an mRNA molecule at the 3'-end thereof a nucleotide sequence heterologous to the nucleic acid molecule comprising at least a portion of the 3'-untranslated region (UTR) of prolactin gene shown in FIG. 2 and selected from the group consisting of nucleotide sequences having SEQ ID NOS: 1, 8, 9, 10, 11, 12 and 14 in Table I and effective to increase the period of translation of said mRNA molecule in a cell, and effecting translation of said mRNA molecule in said cell.

7. The method of claim 1 or 6 wherein said mRNA molecule encodes a protein or peptide.

8. The method of claim 7 wherein said protein or peptide is selected from the group consisting of an enzyme, an antigen, an immunogen, an allergen, an enzyme inhibitor, a hormone, a lymphokine, an immunoglobulin, a toxin, a toxin subunit, a mammalian protein, a structural protein, and a receptor.

9. The method of claim 7 wherein said protein or peptide is selected from the group consisting of bovine preprolactin, human insulin receptor, α-subunit of the canine signal recognition particle receptor, the IgG binding domains of Staphylococcal protein A, HIV gag protein, CAT and RCV gB protein.

10. A method of translation a selected mRNA molecule, which comprises:

coupling to a nucleic acid molecule transcribable to or which itself is an mRNA molecule at the 3'-end thereof a nucleotide sequence heterologous to the nucleic acid molecule comprising the 3'-untranslated region (UTR) of a prolactin gene contained within nucleotide 51 to nucleotide 97 as seen in FIG. 2 (SEQ ID NO:3) and effective to increase the period of translation of mRNA molecule in a cell, and effecting translation of said mRNA molecule in said cell.

11. A hybrid nucleic acid molecule, comprising:

a first nucleotide sequence transcribable to or which is an mRNA molecule, a second nucleotide sequence heterologous to said first nucleotide sequence comprising a Xenopus β-globin 5'untranslated region (UTR) coupled to a translation initiation sequence for said first nucleotide sequence comprising a Kozak consensus ANNAUGG, said second nucleotide sequence being operatively coupled to the 5'-end of said first nucleotide sequence and being effective to increase the rate of translation initiation of the mRNA molecule in a cell, and a third nucleotide sequence heterologous to the first nucleotide sequence comprising at least a portion of a 3'-untranslated region (UTR) of a prolactin gene shown in FIG. 2 selected from the group consisting of nucleotide sequences having SEQ ID NOS: 1, 8, 9, 10, 11, 12 and 14 in Table I, said third nucleotide sequence being operatively coupled to the 3'-end of said first nucleotide sequence and being effective to increase the period of translation of said mRNA molecule in a cell.

12. The nucleic acid molecule of claim 11 further comprising a polyadenylation sequence operatively coupled to the 3'-end of said third nucleotide sequence and effective to stabilize translation of said mRNA molecule independent of said third nucleotide sequence.

13. The nucleic acid molecule of claim 11 wherein said Kozak consensus sequence is ACCAUGG.

14. The nucleic acid molecule of claim 11 wherein said initiation sequence further comprises a Shine-Dalgarno sequence.

15. A hybrid nucleic acid molecule, comprising:

a first nucleotide sequence transcribable to or which is an mRNA molecule, and a second nucleotide sequence heterologous to the first nucleotide sequence comprising at least a portion of a 3'-untranslated region (UTR) of a prolactin gene shown in FIG. 2 and selected from the group consisting of nucleotide sequences having SEQ ID NOS: 1, 8, 9, 10, 11, 12 and 14 in Table I, said second nucleotide sequence being operatively coupled to the 3'-end of said first nucleotide sequence and effective to stabilize translation of said mRNA molecule in a cell.

16. The hybrid molecule of claim 11 or 15 wherein said mRNA molecule encodes a protein or peptide.

17. The hybrid molecule of claim 16 wherein said protein or peptide is selected from the group consisting of an enzyme, an antigen, an immunogen, an allergen, an enzyme inhibitor, a hormone, a lymphokine, an immunoglobulin, a toxin, a toxin subunit, a mammalian protein, a structural protein, and a receptor.

18. The hybrid molecule of claim 17 wherein said protein or peptide is selected from the group consisting of bovine preprolactin, human insulin receptor, α-subunit of the canine signal recognition particle receptor, the IgG binding domains of Staphylococcal protein A, HIV gag protein, CAT and HCV gB protein.

19. A hybrid nucleic acid molecule, comprising:

a first nucleotide sequence transcribable to or which is an mRNA molecule, and a second nucleotide sequence heterologous to the first nucleotide sequence comprising the nucleotide sequence of the 3'-UTR of a prolactin gene contained within nucleotide 51 to nucleotide 97 as seen in FIG. 2 (SEQ ID NO:3) and effective to increase the period of translation of the mRNA molecule in a cell.

* * * * *